(12) United States Patent
Li et al.

(10) Patent No.: US 10,957,970 B2
(45) Date of Patent: Mar. 23, 2021

(54) SYSTEMS AND METHODS FOR INCORPORATING A PATCH ANTENNA IN AN IMPLANTABLE MEDICAL DEVICE

(71) Applicant: PACESETTER, INC., Sylmar, CA (US)

(72) Inventors: Perry Li, Arcadia, CA (US); Lequan Zhang, La Crescenta, CA (US)

(73) Assignee: Pacesetter, Inc., Sylmar (CA)

( * ) Notice: Subject to any disclaimer, the term of this patent is extended or adjusted under 35 U.S.C. 154(b) by 239 days.

(21) Appl. No.: 15/255,985

(22) Filed: Sep. 2, 2016

(65) Prior Publication Data
US 2018/0069303 A1    Mar. 8, 2018

(51) Int. Cl.
| | | |
|---|---|---|
| *H01Q 1/27* | (2006.01) | |
| *H01Q 9/04* | (2006.01) | |
| *H01Q 1/48* | (2006.01) | |
| *H01Q 1/22* | (2006.01) | |
| *A61N 1/372* | (2006.01) | |

(52) U.S. Cl.
CPC ......... *H01Q 1/273* (2013.01); *A61N 1/37229* (2013.01); *H01Q 1/2291* (2013.01); *H01Q 9/0407* (2013.01); *H01Q 9/0421* (2013.01); *H01Q 9/0442* (2013.01)

(58) Field of Classification Search
CPC .... H01Q 1/273; H01Q 1/2291; H01Q 9/0407; H01Q 9/0421; H01Q 9/0442; A61N 1/37229
USPC ........................................................ 607/156
See application file for complete search history.

(56) References Cited

U.S. PATENT DOCUMENTS

| | | | |
|---|---|---|---|
| 2005/0134520 A1* | 6/2005 | Rawat ................ | A61N 1/37229 343/873 |
| 2010/0109958 A1* | 5/2010 | Haubrich ........... | A61N 1/37229 343/718 |
| 2012/0306721 A1* | 12/2012 | Okegawa ............. | H01Q 9/0421 343/905 |
| 2014/0062794 A1* | 3/2014 | Guo ..................... | H01Q 9/0414 343/700 MS |
| 2016/0301239 A1* | 10/2016 | Funderburk ......... | H02J 7/0036 |

* cited by examiner

*Primary Examiner* — Erin M Piateski
(74) *Attorney, Agent, or Firm* — Polsinelli PC

(57) ABSTRACT

Systems and methods for an implantable medical device which utilizes a patch antenna for communicating with an external device. The implantable medical device includes a housing, a header, and a patch antenna formed using an RF plate and a ground plate, which may be or include a metal surface of the housing. Also, a material of the header forms a dielectric of the patch antenna.

8 Claims, 8 Drawing Sheets

SYSTEMS AND METHODS FOR INCORPORATING A PATCH ANTENNA IN AN IMPLANTABLE MEDICAL DEVICE

FIELD OF THE INVENTION

Aspects of the present invention relate to medical apparatus and methods. More specifically, the present invention relates to systems and methods for implementing a patch antenna on an implantable medical device.

BACKGROUND OF THE INVENTION

Implantable pulse generators (IPGs) come in a variety of forms for different applications. For example, some IPGs, such as pacemakers and implantable cardioverter defibrillators (ICDs), are used in the treatment of cardiac conditions. Other IPGs, such as neuromodulators or neurostimulators, are used in chronic pain management or the actuation and control of other body systems. These devices, which are known as implantable medical devices (IMDs), commonly include a housing (i.e., can), feedthrus, and a connector assembly that is enclosed in a header. Electrical stimulation originating in the housing is led to the connector assembly through the feedthrus. The connector assembly serves to transmit electrical signals out of the implantable medical device and to a lead electrically connected to the connector assembly, the lead transmitting electrical signals between the implantable medical device and patient tissue.

IMDs often communicate with an external unit while the device is still implanted. Traditional wireless implantable devices have used inductive telemetry to communicate. However, an inductive interface requires a relatively short distance (on the order of centimeters) between the implanted device and the extracorporal unit with which it communicates. This, in turn, may be inconvenient for the patient as well as impractical for the personnel conducting the procedure. Moreover, the maximum data rate for an inductive interface is relatively low, which results in practical limitations as to the amount of data that can be communicated.

Still other wireless implantable devices use the MICS (Medical Implant Communication Service) frequency band of 402-405 MHz. At this frequency, antennas need to be relatively large compared to the size of the header in order to function well. This has led to the widespread use of wire type antennas such as the monopole (open loop), closed loop, or inverted F. These antennas have proven to be very versatile with their ability to conform to the shape of the header and route around bore holes and lead connectors. However, this means that any changes to an existing or new header on the IMD can lead to significant or complete redesigns of the antenna. Also, header sizes may have to grow in height to accommodate these antennas.

Therefore, there is a need in the art for a communication system for IMDs which is small enough to fit within a device header.

SUMMARY

The communication arrangements and methods disclosed herein allow for a patch antenna which can be made small enough to fit in a device header, where advantages over monopole and loop antennas can be utilized to improve RF performance and communication range.

Recently, Bluetooth Low Energy (BLE) communication operating at 2.40-2.48 GHz has been found to be a reliable means of RF communication in implantable medical devices. The introduction of BLE communications opens the door for a different type of antenna to be used in implantable devices, specifically, a patch antenna. Because the size of the patch antenna is inversely proportional to the operating frequency, the higher BLE frequency means the size of the antenna can be decreased significantly to a size that is more reasonable for a device header. Previously, with MICS communication, the only way to accommodate the large patch antenna size was to place the antenna on the broad side of the housing, such as described in U.S. Patent Application 2003/0216793 (incorporated herein by reference in its entirety). However, placing an antenna on the side of the housing is not ideal for a variety of reasons, such as lack of manufacturing feasibility as well as durability of an exposed antenna when implanted.

A basic patch antenna is made up of two rectangular metal plates. One plate, normally on the bottom, is the ground and the other top plate is the signal. In between the two plates is a dielectric material. In some embodiments disclosed herein, the patch antenna employs a single plate and uses a metal surface of the housing (i.e., can) and/or an extension member extending therefrom to act as the ground plate. The header material can serve as the dielectric between the two metal surfaces of the two plates. Using the housing surface allows the antenna to be smaller, able to be enclosed within the header, and easier to manufacture than a conventional two-piece patch. Employing the material of the header as the dielectric for the patch antenna also saves space and simplifies manufacturing. Such configurations, at Bluetooth frequencies, allow the patch antenna to take up a smaller cross sectional area than other antennas, such as the monopole and loop antennas.

In additional to being smaller than other antennas, it is also easier to tune the critical parameters of a patch antenna such as frequency, bandwidth, and impedance. Since the RF plate forms a capacitor with the can surface, the dimensions, shape, and height of the RF plate determine those critical parameters. In addition, the basic patch antenna can take on several different implementations in order to decrease size and improve flexibility if space within the header is tight. Some of these implementations will be described in detail and shown in the drawings.

In one embodiment, an implantable medical device has a housing of electronics, a header, and a patch antenna. The housing is coupled to the header and encloses a connector assembly. A polymer material of the header surrounds or is otherwise associated with the connector assembly. The patch antenna can be formed by electrically connecting a plate to the electronics contained within the housing. This electrical connection can, for example, occur via an RF pin using a feedthru in the metal surface of the housing. The plate and metal surface together form the patch antenna, with the metal surface acting as a ground plate of the antenna.

The header can cover, enclose, or otherwise encapsulate the plate, thereby protecting the antenna from outside elements and contamination. In addition, the header material can form the dielectric of the patch antenna, being formed such that the header material is located between the plate and the metal surface.

In one configuration, the patch antenna can be shorted to the metal surface by connecting a ground pin to an opposite portion of the plate from where the RF pin connects.

The implantable medical device can, for example, communicate in a Bluetooth™ frequency band via the patch antenna. For example, the patch antenna can communicate in frequencies including 2.40 to 2.48 GHz.

The orientation and location of the patch antenna with respect to the housing can vary among configurations. For example, in one configuration, the patch antenna can have a planar orientation which is parallel to the planar orientation of the portion of the housing assembly which connects to the header connector assembly. In another configuration, the patch antenna can have a planar orientation which is perpendicular to the planar orientation of the portion of the housing which connects to the header connector assembly. In such a vertical orientation, a metal flap or surface can likewise be formed to be vertically parallel to the plate, thereby forming the ground plate of the patch antenna. This vertical patch antenna can, for example, be useful where the header has more space in the vertical direction than the horizontal direction.

In yet another configuration, the metal surface forming the ground plate of the patch antenna can be folded around the radiating plate, effectively doubling the size of the original patch antenna.

In another embodiment, an implantable medical device can have a housing assembly which encloses electronics and which has a metal surface with a feedthru opening. The implantable medical device can also have a patch antenna made of a plate electrically connected to the electronics via a pin extending through the feedthru opening.

In one configuration of such an embodiment, a header assembly can be attached to the housing assembly, where the header assembly encloses the patch antenna. The patch antenna can be formed using the plate and the metal surface of the housing assembly, where the metal surface forms a ground plate. In some configurations, the header material which forms the header assembly can be used as a dielectric for the patch antenna, with the dielectric being located between the plate and the metal surface.

In some configurations, rather than using a metal surface of the housing assembly to form the ground plate of the patch antenna, a feedthru flange can be used as a ground plate. This feedthru flange can be, together with the plate, oriented vertically with respect to the pin which is electrically connected to the electronics.

If no flange is used, the plate will likely be in a perpendicular orientation with respect to the pin such that the patch antenna is formed in a parallel planar orientation with respect to the housing assembly.

An exemplary method embodiment for manufacturing the implantable medical devices described herein could include: identifying a resonance frequency for communications between an implantable medical device and an exterior device, the implantable medical device comprising: an housing having a metal surface and enclosing electronics, the metal surface having a feedthru opening; a patch antenna comprising a plate electrically connected to the electronics via a pin extending through the feedthru opening, the metal surface of the housing forming a ground plate for the patch antenna; and a header attached to the housing, the header enclosing the patch antenna; and modifying, based on the resonance frequency, at least one of a plate size of the plate, a shape of the plate, a distance between the plate and the metal surface, a location of the feedthru opening, and a length of the pin. The patch antenna can also be shorted to the metal surface by a second pin at an opposite edge of the plate from the pin.

The modifying can alter at least one of a capacitance and an inductance associated with the patch antenna. In addition, the header can be formed using a header material, where the header material serves as the dielectric for the patch antenna. The type of header material used would, in such configurations, modify the resonance frequency, and accordingly the method can further include modifying or otherwise selecting the header material based on the resonance frequency identified.

A second method embodiment directed to manufacturing an implantable medical device can include forming a patch antenna of the implantable medical device by delivering a material between an RF plate of the patch antenna and a ground plate of the patch antenna, the material acting as a dielectric of the patch antenna and also forming a header that encloses a connector assembly of the implantable medical device.

Disclosed herein is an implantable medical device. In one embodiment, the device includes a header connector assembly and a patch antenna. The header connector assembly includes a connector assembly and a header enclosing the connector assembly. The housing is coupled to the header connector assembly and includes a metal surface. The housing encloses electronics for the implantable medical device. The patch antenna is enclosed by the header and includes an RF plate and a ground plate. A material forming the header serves as a dielectric of the patch antenna.

In one embodiment, the RF plate is electrically connected to the electronics via an RF conductor through a feedthru in the metal surface. The RF conductor may attach to a first rectangular edge of the plate, and a ground conductor may short the patch antenna to the metal surface by electrically connecting a second rectangular edge of the plate to the metal surface, the second rectangular edge being opposite to the first rectangular edge.

In one embodiment, the patch antenna uses the metal surface as the ground plate. The patch antenna may communicate in a Bluetooth frequency band. The Bluetooth frequency band may be contained within 2.40 to 2.48 GHz.

In one embodiment, the patch antenna may have a planar orientation which is parallel to the metal surface. The patch antenna may use the metal surface as the ground plate.

In one embodiment, the metal surface may include an extension member extending from the metal surface. The extension member may form the ground plate. The metal surface may form a first ground plate and the extension member may form a second ground plate. The extension member and the planar orientation of the patch antenna may be perpendicular to a planar orientation of the metal surface immediately adjacent the RF plate.

In one embodiment, the extension member may be folded around the plate. The plate may be sandwiched between the extension member and metal surface.

In one embodiment, the RF plate and the ground plate are spaced apart from the adjacent metal surface. The ground plate may wrap around the RF plate such that the RF plate is sandwiched between offset parallel first and second portions of the ground plate. The RF plate and the ground plate may be parallel with the metal surface immediately adjacent the RF plate. Alternatively, the RF plate and the ground plate are not parallel with the metal surface immediately adjacent the RF plate.

In one embodiment, the material may include at least one of a thermosetting polymer, an epoxy, thermoplastic, polyurethane, tecothane, pellethane, silicone, acrylic, or bionate.

In one embodiment, the dielectric material used by the patch antenna is distinct from the material used by the header. In such a scenario, the patch antenna is formed with a first material between the RF plate and the ground plate, at which point the header is formed around the completed patch antenna using a second material.

Also disclosed herein is a method of manufacturing an implantable medical device. In one embodiment, the method includes forming a patch antenna of the implantable medical device by delivering a material between an RF plate of the patch antenna and a ground plate of the patch antenna, the material acting as a dielectric of the patch antenna and also forming a header that encloses a connector assembly of the implantable medical device.

In one embodiment of the method, the material may include at least one of a thermosetting polymer, an epoxy, thermoplastic, polyurethane, tecothane, pellethane, silicone, acrylic, or bionate. Also, the material may be delivered via at least one of injection or casting.

In one embodiment of the method, the ground plate may include a metal surface of a housing of the implantable medical device, the housing enclosing electronics of the implantable medical device and operably coupled to the header.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

Implementations of the present disclosure involve an implantable medical device (IMD) for communication with an external unit using a patch antenna. The IMD generally includes a housing for electronics and a header, the header allowing the electronics within the housing to interact with the implanted organism via leads and other mechanisms. The patch antennas disclosed herein are sized such that they can fit within the header assembly, and can utilize the top surface of the can (the housing assembly) as a ground plate. Advantages of the disclosed configurations and methods include a smaller antenna profile compared to alternative communication mechanisms, where modifications to the header design will have less impact on the antenna design. In addition, the resonant frequency of the patch antenna can be adjusted for specific circumstances and designs, and provides improved radiation efficiency.

Patch antennas disclosed herein use a sheet of metal, or patch, that is parallel with the can surface. The patch is held a specified distance away from the can using the header material in-between to serve as the dielectric medium. The patch plate is welded to a feedthru pin which connects the antenna to the RF circuit inside the can. Since the can surface serves as the antenna ground, it must also be connected to the RF circuit ground on the device. In a most basic implementation, the patch plate is a single square or rectangular sheet of metal that forms a capacitor with the can ground. For patch antennas, the RF signal is fed at a specific location on the patch and then radiated through the fringing electric fields formed between the edges of the plate and the can surface below. Due to these fringing fields, the patch plate must always be smaller than the size of the can surface.

Patch antenna design allows for the antenna and can to be represented as a capacitor (patch) in series with an inductor (feedthru pin) to create a resonance point. To change the resonance frequency, a few parameters can be modified such as patch plate size and shape, distance between patch plate and can, location of the feedthru pin connection to the patch plate, and length of the feedthru pin. Each of these parameters will alter either the capacitance or inductance of the antenna therefore shifting the resonance frequency.

Several different implementations can be made to make the basic patch antenna smaller and more flexible. In one embodiment, the RF plate of the patch antenna can be shorted to ground in order to change the current distribution around the patch plate and effectively decrease its size. The shorting pin also adds an extra inductive element to aid in tuning the antenna to the correct resonance frequency.

Figure 1:
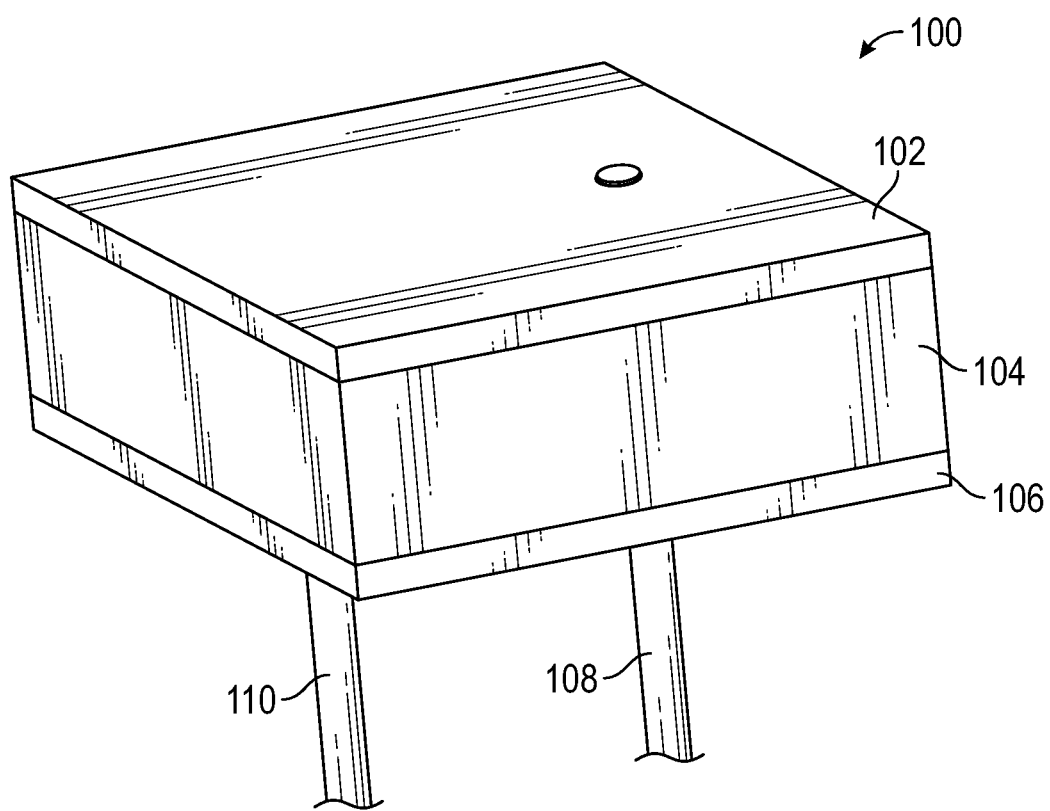
FIG. 1 is an isometric view of an exemplary patch antenna.

FIG. 1 illustrates an isometric view of an exemplary patch antenna 100. A patch antenna 100 is made up of two rectangular metal plates 102, 106. One plate 106, illustrated on the bottom, is the ground and the other top plate 102 is the signal or RF plate. In between the two plates is a dielectric material 104. At Bluetooth™ frequencies, the patch antenna can be designed to take up a smaller cross sectional area than other antennas such as the monopole and loop antennas. The signal is fed to the top plate 102 via an RF conductor (e.g., RF pin) 108, and the ground plate 106 is grounded using a grounding conductor (e.g., pin) 110.

In addition to being smaller than other antennas, it is also easier to tune the critical parameters of a patch antenna such as frequency, bandwidth, and impedance. Because the patch forms a capacitor with the can surface, the dimensions, shape, and height of the patch plate determine those critical parameters. In addition, a patch antenna 100 can take on several different implementations in order to decrease size and improve flexibility if space within the header is tight. Some of these implementations will be described in detail below.

Figure 2A:
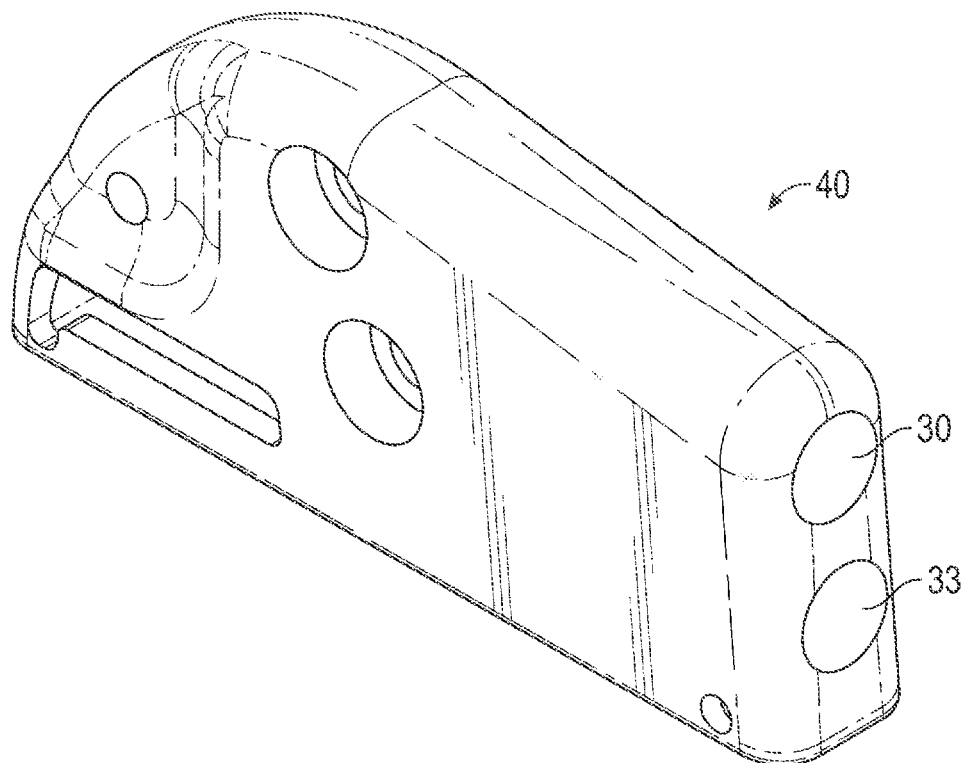
FIG. 2A is an isometric view of a representative header.
Figure 2B:
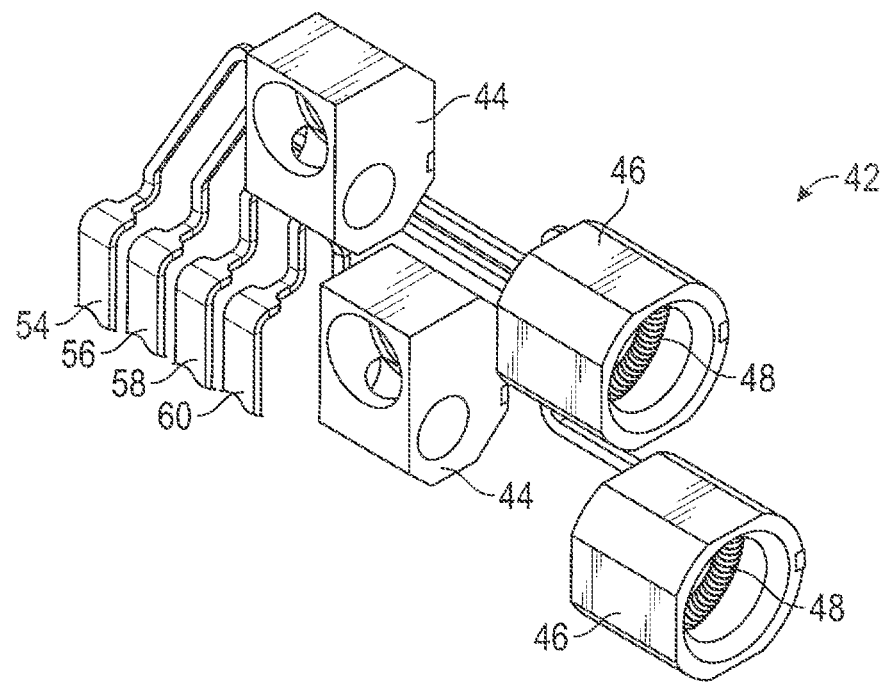
FIG. 2B is an isometric view of a representative connector assembly used with the header of FIG. 2A to form a header connector assembly.

FIG. 2A is an isometric view of a representative header 40 and FIG. 2B is an isometric view of a representative connector assembly 42. The header 40 of FIG. 2A has two receptacles 30 and 33. However, in other embodiments, the header 40 of FIG. 2A may have two or more receptacles. These receptacles 30 and 33 can be used to for leads and other mechanisms for an IMD to interact with an organism in which the IMD is implanted.

As illustrated in FIG. 2B, the connector assembly 42 includes tip blocks 44 and ring blocks 46. The ring blocks 46 include spring contacts 48. Each electrical block 44 and 46 of the connector assembly 42 serves as an electrical contact of the connector assembly 42. Thus, each tip block 44 is configured to receive and make electrical contact with the tip terminal of a lead connector end received in the corresponding receptacle 30, 33 of the header 40. Similarly, each ring block 46 is configured to receive and make electrical contact with the ring terminal of a lead connector end received in the corresponding receptacle 30, 33 of the header 40. While the connector assembly 42 of FIG. 2B is of an IS-1 configuration, other configurations (e.g., IS-4, etc.) can be used in other embodiments. While the connector assembly 42 of FIG. 2B only depicts two pairs of blocks 44, 46, in other embodiments where the header includes more than a single pair of receptacles 30, 33 (e.g., more than a single pairs of receptacles 30, 33), such that the connector assembly 42 will have a multiple pairs of blocks 44, 46.

As shown in FIG. 2B, the connector assembly 42 also includes an A-tip tab 54, an A-ring tab 56, an RV-ring tab 58, an RV-tip tab 60, and other conductors that extend between the various tabs and their respective electrical contacts of the connector assembly or other components thereof. The various tabs are welded to corresponding terminals extending from circuitry of the IMD. The connector assembly 42 is manufactured of materials and via methods known in the industry. The connector assembly 42 is molded into the header 40 to form the header connector assembly, which sits on top of and is coupled to the housing.

Figure 3A:
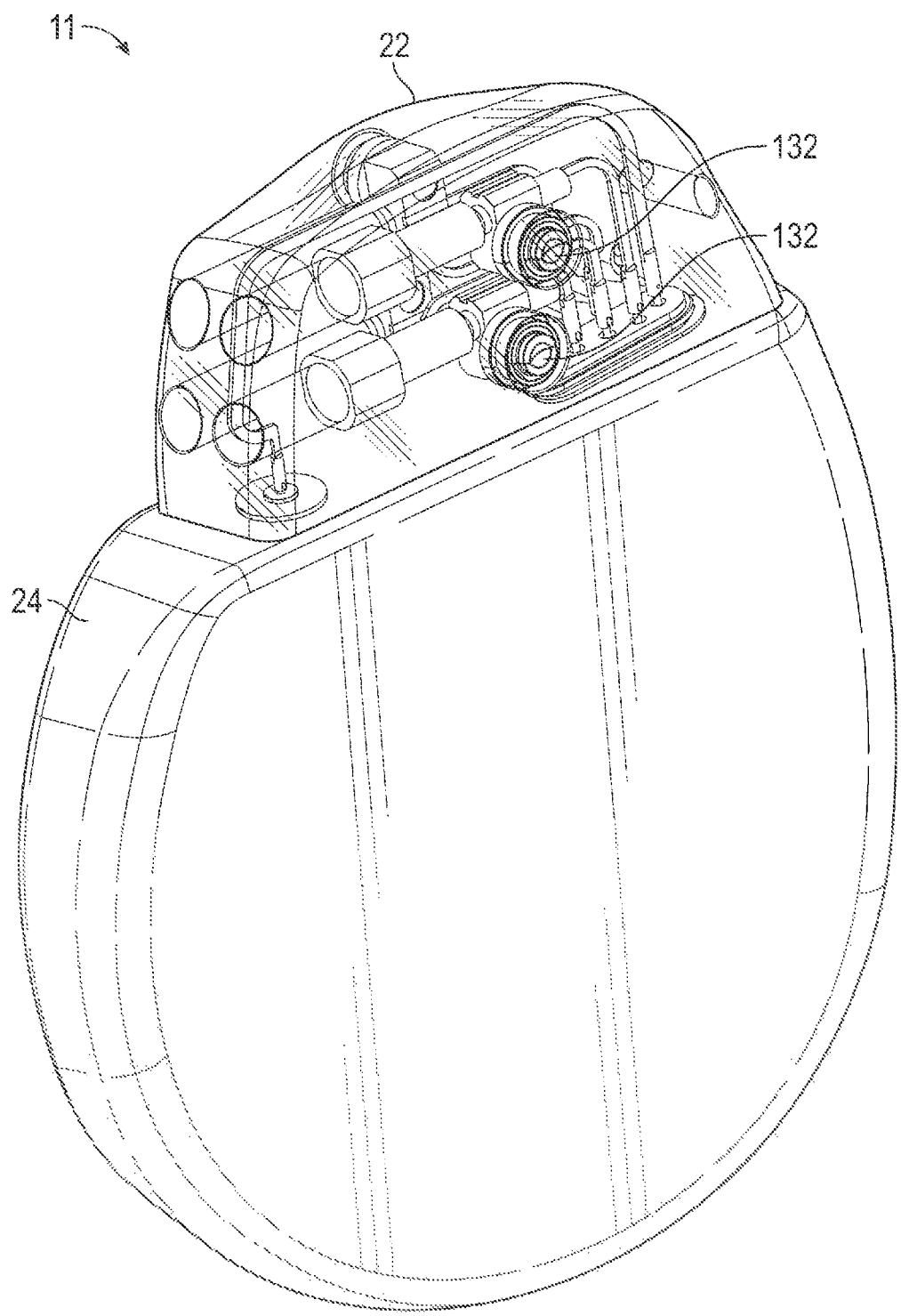
FIG. 3A is an isometric view of an IMD.
Figure 3B:
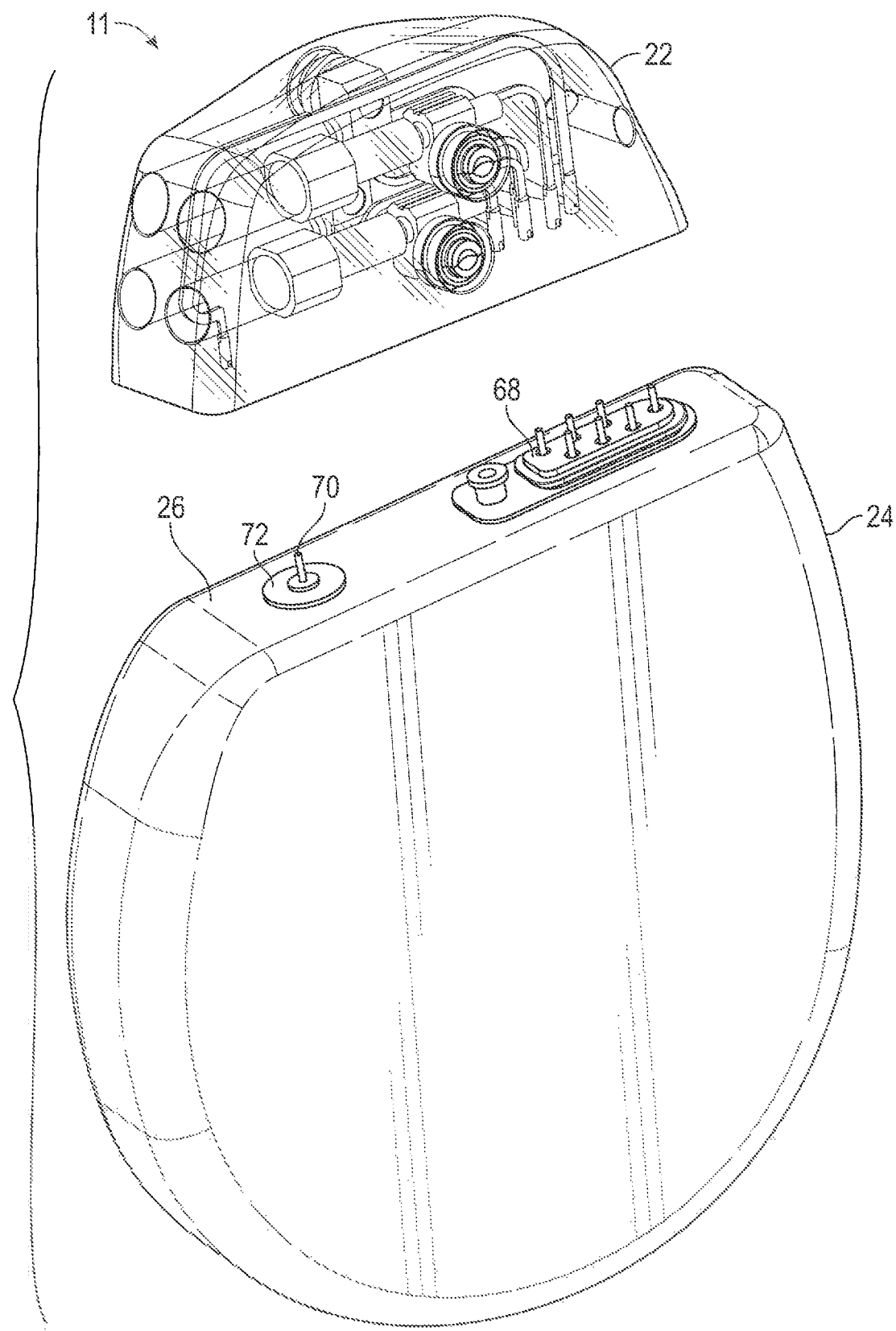
FIG. 3B is an exploded isometric view of the same IMD, wherein the header connector assembly is spaced apart from the housing.

FIG. 3A is an isometric view of an IMD 11, and FIG. 3B illustrates the same IMD 11, but with the header connector assembly 22 spaced apart from the housing 24.

As depicted in FIG. 3B, a feedthru 68 and an RF pin 70 with their associated terminals extend outwardly from a top surface 26 of the housing 24 from their respective connections to the electronic circuitry contained within the confines of the housing 24. The RF pin 70 is surrounded by a round metal surface 72, which is the feedthru flange and which is connected to the can/ground. There can also be a piece of ceramic between the RF pin 70 and the feedthru flange 72, which provides electrical isolation between the RF pin 70 and the feedthru flange 72. In other configurations, the feedthru flange 72 can have alternative shapes, preferably a rectangle with a size larger than the RF plate used as a patch antenna. The wires of the feedthru 68 are welded to their respective tabs 54, 56, 58, and 60, discussed above with respect to FIG. 2B, as well as the patch antenna RF plate to be further discussed.

Figure 4A:
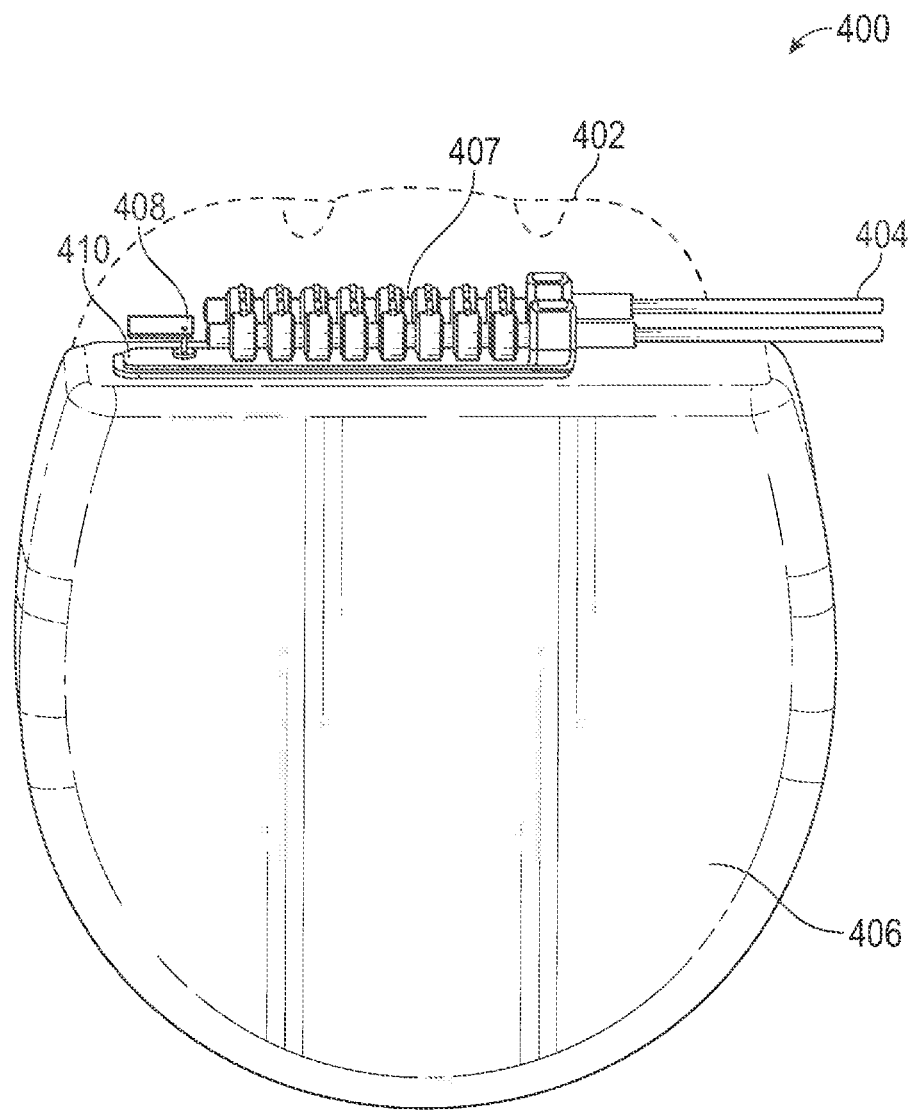
FIG. 4A is an isometric view of an IMD having a patch antenna on a housing with an alternative header design.

FIG. 4A is an isometric view of an IMD 400 having a patch antenna 408 on a housing 406 with a connector assembly 407 from that illustrated in FIGS. 2A-3B. In addition, the header 402 is illustrated with dashed lines, with leads 404 extending from the IMD. In this configuration, the IMD 400 has a feedthru flange 410 on the metal surface of the housing 406 beneath the connector assembly 407. The feedthru flange 410 can have multiple layers and can be electrically connected to the metal surface of the can. A plate 408 of a patch antenna is likewise illustrated and is sized such that the plate 408 is contained within the header 402. When the plate 408 receives an RF signal from electronics within the housing 406, the plate, the polymer material forming the header 402, and the metal surface of the can (including anything grounded to the can, such as the feedthru flange 410) together form a patch antenna, allowing the signal to be communicated to an external device.

Figure 4B:
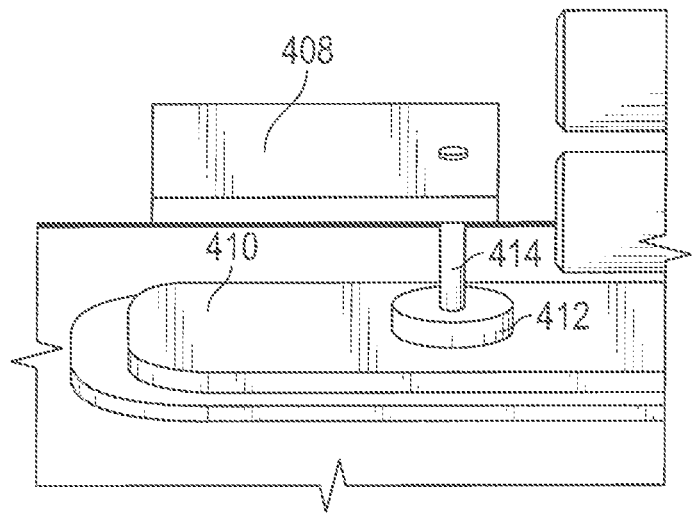
FIG. 4B is a close up view of the patch antenna illustrated in FIG. 4A.

FIG. 4B is a close up view of the patch antenna illustrated in FIG. 4A. With the close up view, the RF pin 414 and feedthru 412 which connect the plate (also known as the RF plate) 408 are visible. The RF pin 414 electrically connects the plate 408 to the electronics internal to the housing 406. The feedthru plate 412 electrically isolates the RF pin 414 from the exterior of the housing, including the metal surface of the housing (and the feedthru flange 410). As stated before, a patch antenna is formed between the plate 408 and the metal surface, with the metal surface acting as a grounding plate when the plate 408 receives a signal from the electronics of the housing 406. The polymer material (not shown) forming the header 402 acts as the dielectric between the two electrically conductive surfaces of the patch antenna. The polymer material can be in the form of a thermoset polymer (e.g., epoxy) or an injectable polymer such as, for example, polyurethane, tecothane, pellethane, bionate, silicone, acrylic, or etc. The header material that encloses the connector assembly forms the header and acts as the dielectric for the patch antenna can be any type of thermoplastic, or any other variety of material that can be caused to flow about and between the various elements of the antenna and connector assembly to form the header that encases these electrically conductive components.

Figure 4C:
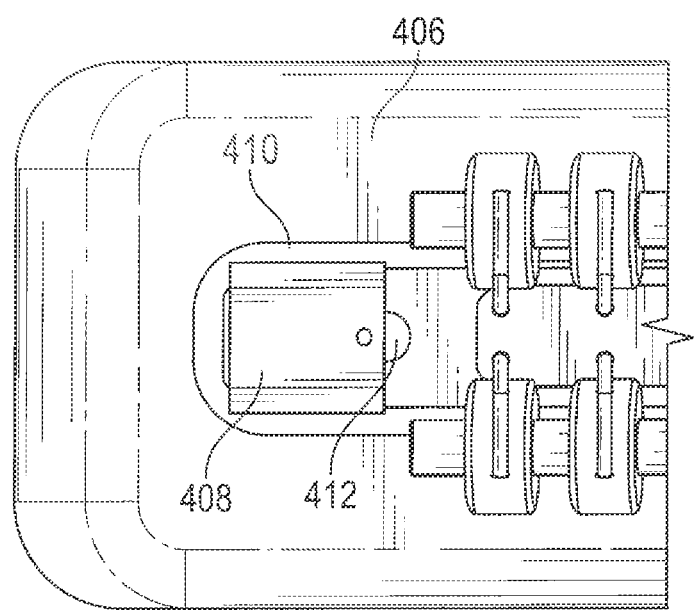
FIG. 4C is a rotated view of the patch antenna illustrated in FIG. 4A.

FIG. 4C is a rotated view of the patch antenna illustrated in FIG. 4A, similarly showing the plate 408, the feedthru 412, the feedthru flange 410 on the metal surface of the housing 406, and the housing 406 itself. In this illustration, the plate 408 is illustrated as centered over the housing 406, however in other configurations the plate 408 can be moved or located as required for specific functionality. For example, the plate 408 could be moved closer to the left edge of the housing 406, or could be closer to the top or bottom edge of the illustrated housing 406, such that the plate and the resulting patch antenna are not centered on the IMD.

Figure 5:
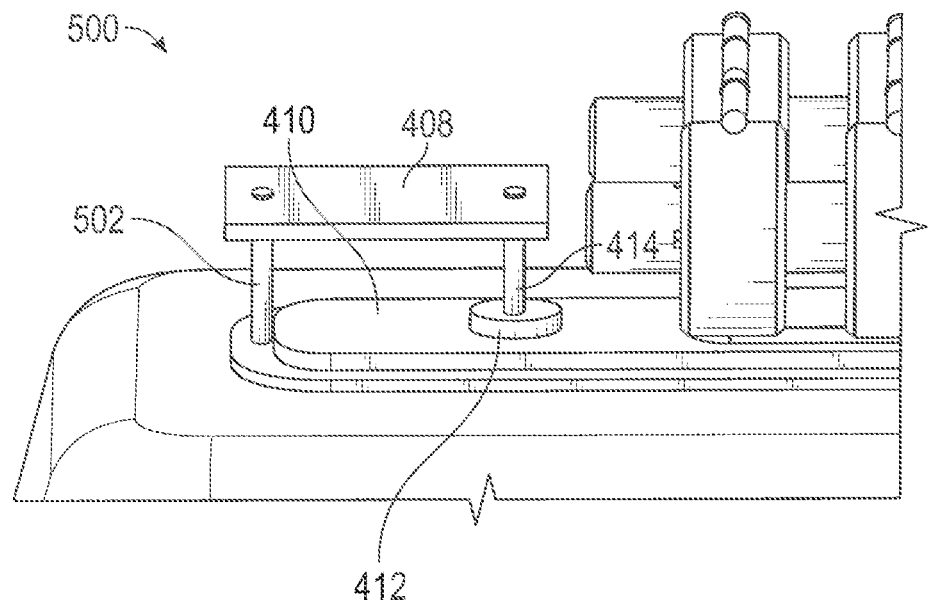
FIG. 5 is an isometric view of an exemplary shorted patch antenna.

FIG. 5 is an isometric view 500 of an exemplary shorted patch antenna. In this example configuration, the patch antenna can be shorted to ground in order to change the current distribution around the patch plate 408 and effectively decrease its size. The shorting pin 502 can also add an extra inductive element to aid in tuning the antenna to the correct resonance frequency. As illustrated, the shorting pin 502 is on the opposite end of the rectangular patch panel 408 from the RF pin 414. Moreover, the shorting pin 502 is electrically connected to the metal surface of the can 406, either directly or (as illustrated) by shorting to the feedthru flange 410.

Figure 6:
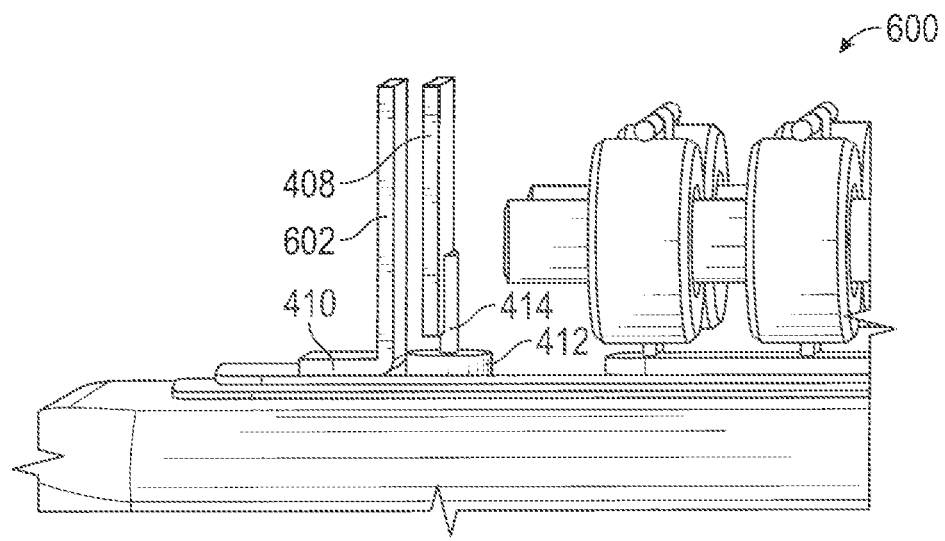
FIG. 6 illustrates an isometric view of a patch antenna in a vertical orientation.

The patch antenna is not required to be parallel to the surface of the can. FIG. 6 illustrates an isometric view 600 of a patch antenna in a vertical orientation, where the plate 408 is oriented vertically parallel to a ground plate 602 (flange) which is also oriented vertically. The ground plate 602 is electrically connected to the metal surface of the can (either directly or, as illustrated, by connection with the feedthru flange 410) and continues to act as the grounding plate for the patch antenna. The vertical ground plate 602 may be an extension member 602 of the metal surface and may take the form of a flange, tab, or other structure projecting from the metal surface.

Figure 7:
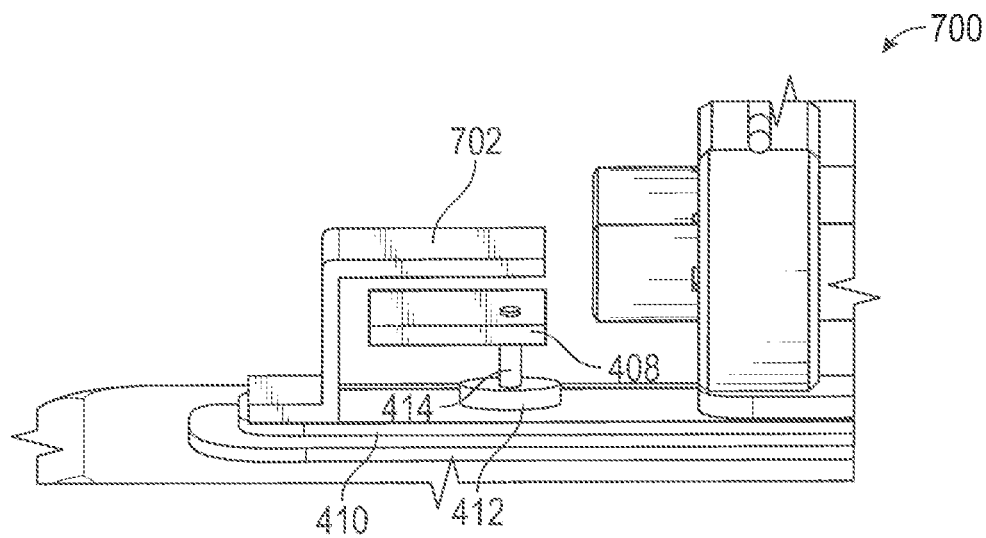
FIG. 7 illustrates an isometric view of a folded patch antenna with a ground plate folded around the RF plate and a ground plate using the metal surface of the can.

FIG. 7 illustrates an isometric view 700 of a folded patch antenna with a ground plate 702 folded around the RF plate 408 and sandwiching the RF plate 408 between the folded ground plate 702 and a second ground plate in the form of the metal surface of the can (and/or the feedthru flange 410). The folded ground plate 702 may be an extension member 702 of the metal surface and may take the form of a flange, tab, or other structure projecting from the metal surface. Because the RF plate 408 will, in this configuration, have two separate but electrically connected ground plates (the folded flange 702 and the metal surface of the can), the effective size of the patch antenna is doubled. This allows the patch antenna to decrease in size along the width and length, and instead grow taller. Such a configuration can, for example, be useful in configurations where the width and/or length of the patch antenna is limited, but the header is high enough to accommodate a taller antenna structure.

Figure 8:
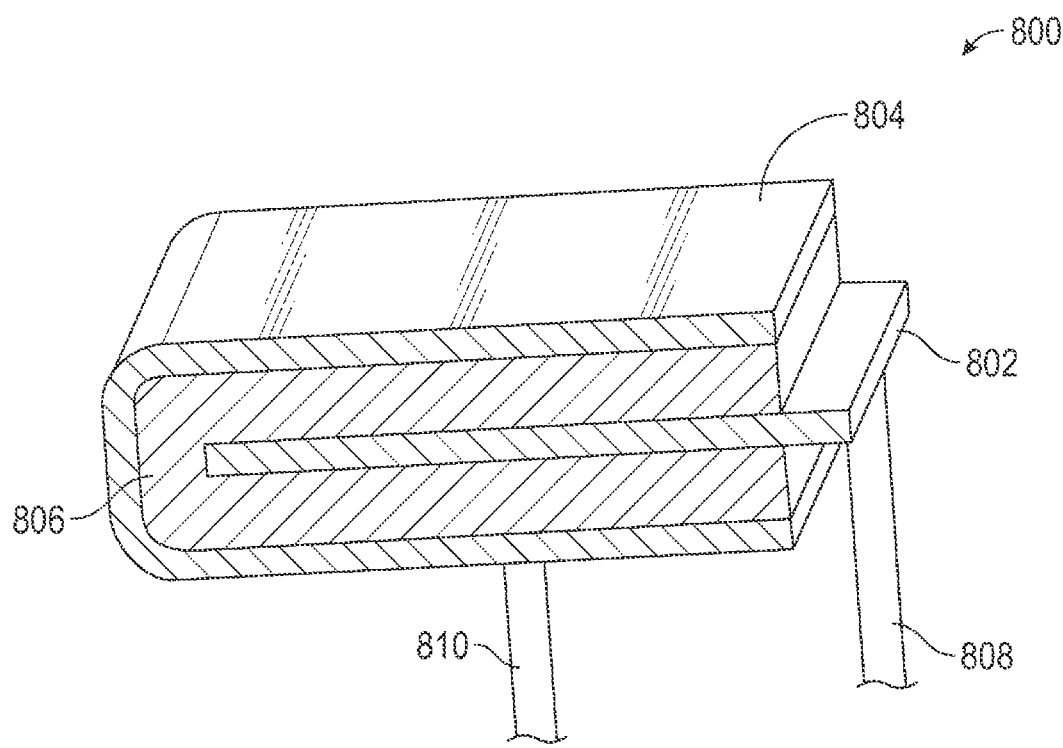
FIG. 8 illustrates an isometric view of a folded patch antenna with a ground plate folded around the RF plate where the ground plate is not the metal surface of the can.

FIG. 8 is an isometric view of a second example of a folded patch antenna. As illustrated in FIG. 8, a folded patch antenna 800 has a ground plate 804 folded around the RF plate 802, and the RF plate 802 and the ground plate 804 are separate by a dielectric 806. This dielectric material 806 could be separately applied from the dielectric material of the housing or could be the dielectric material of the housing. As illustrated, the patch antenna 800 is physically separated from the can and instead is grounded using a grounding pin 810 between the ground plate 804 and a grounding source on the IMD. Like other configurations previously discussed, the RF plate 802 receives the signals from electronics via an RF pin 808.

It should be noted, that while the dielectric material between the surfaces of the plates of the patch antennas discussed herein with respect to FIGS. 4A-7 is not shown in FIGS. 4A-7, these embodiments will have a dielectric material that occupies all of the space between the surfaces of the plates similar to the dielectric material 104, 806 depicted in FIGS. 1 and 8, whether the plate be an RF plate or a ground plate. Moreover, such dielectric material for the embodiments of FIGS. 4A-8 may be provided via the polymer material that forms the housing that encloses the connector assembly, as can be understood from FIGS. 2A-3B. Such dielectric material may completely enclose and encapsulate each plate, effectively isolating each plate surface from the surfaces of the other plates except for intentional electrical pathways provided by conductor pins, circuits or an extension of an extension member from the metal surface of the housing. Thus, in one embodiment, an IMD as described herein may be manufactured by: electrically connecting the connector assembly to the corresponding circuits of the electronics in the housing; assembling the plates of the patch antenna onto the housing such that the patch antenna plates are electrically connected to the corresponding circuits of the electronics in the housing; and forming the housing about the connector assembly and the antenna plates such that the polymer material of the housing forms the dielectric of the patch antenna, the forming being provided by injection, casting or other methods.

It is also noted that in certain embodiments, the dielectric material used by the patch antenna can be distinct from the material used to form the header. In such embodiments, the patch antenna is formed with a first material between the RF plate and the ground plate, then the header is formed around the completed patch antenna using a second material.

In one embodiment, the implantable medical device may be designed and manufactured as follows. A manufacturer would identify a resonance frequency for communications between an implantable medical device and an exterior device. Such an implantable medical device may include a housing assembly having a metal surface and enclosing electronics. The metal surface may have a feedthru opening, and may be electrically connected to a feedthru flange containing the feedthru opening. A patch antenna of the implantable medical device may include a plate electrically connected to the electronics via a pin extending through the feedthru opening. The metal surface of the housing (and any electrically connected feedthru flange) may form a ground plate for the patch antenna, with the result being that the entire surface of the housing can be considered the ground plate. A header assembly may be attached to the housing assembly and enclose the patch antenna. A polymer material may form the dielectric between the surfaces of the patch antenna. The polymer material in some embodiments is the polymer material that forms the header and encloses the connector assembly. With such an implantable medical device, the manufacturer would then modify, based on the resonance frequency, at least one of a plate size of the plate, a shape of the plate, a distance between the plate and the metal surface, a location of the feedthru opening, or a length of the pin. The modifying may alter at least one of a capacitance or an inductance associated with the patch antenna. The header material may be modified based on the resonance frequency. The plate of the patch antenna may be shorted to the metal surface by a second pin at another location of the plate away from the pin (such as an opposite edge of the RF plate).

The patch antenna can, in various configurations, communicate in a Bluetooth™ frequency band, including 2.40 to 2.48 GHz. The patch antenna can have a planar orientation which is parallel to the metal surface of the housing assembly or can be perpendicular (i.e., vertical) to the metal surface of the housing and rely on a flange or other piece of bent metal to form the ground plate of the antenna. The patch antenna can have a single ground plate or multiple ground plates, and in some configurations the multiple ground plates can be formed using a single grounded piece of metal which is folded around an RF plate. Similarly, the patch antenna can be shorted, such that the grounding pin is on another location or portion of the RF plate away from the RF pin providing a signal to the RF plate.

Once the antenna has the desired resonance frequency, the header can be applied such that the patch antenna is covered by the header. The header material of which the header is made can act as a dielectric for the patch antenna. Because the dielectric affects the antenna performance, the choice of header material used for the header can be made based on the resonance frequency.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:
1. An implantable medical device comprising:
a header connector assembly comprising a connector assembly and a header enclosing the connector assembly, the header including a dielectric material;
a housing coupled to the header connector assembly and comprising a metal surface, the housing enclosing electronics for the implantable medical device; and a modular feedthru assembly comprising:
- a feedthru flange coupled to the housing and electrically connected to the metal surface;
- a radio frequency (RF) plate;
- an RF conductor coupled to the RF plate and electrically connecting the RF plate to the electronics through a feedthru extending through the feedthru flange, the RF conductor being electrically isolated from the feedthru flange and the metal surface; and
- a ground conductor extending between the RF plate and the feedthru flange, the ground conductor directly coupling the RF plate to the feedthru flange and shorting the RF plate to the feedthru flange, wherein the RF plate, the feedthru flange, and a portion of the dielectric material extending between the RF plate and the feedthru flange form a patch antenna, the feedthru flange forming a ground plate of the patch antenna extending parallel to at least a portion of the RF plate.

2. The implantable medical device of claim 1, wherein the RF conductor attaches to a first rectangular edge of the RF plate, and wherein the ground conductor attaches to a second rectangular edge of the RF plate, the second rectangular edge being opposite to the first rectangular edge.

3. The implantable medical device of claim 1, wherein the patch antenna communicates in a Bluetooth frequency band contained within 2.40 to 2.48 GHz.

4. The implantable medical device of claim 1, wherein the patch antenna has a planar orientation which is parallel to the metal surface and the ground plate further includes the metal surface.

5. The implantable medical device of claim 1, wherein the feedthru flange forms a first ground plate and the implantable medical device further comprises an extension member extending from the metal surface, the extension member further forming a second ground plate.

6. The implantable medical device of claim 5, wherein the extension member and the planar orientation of the patch antenna are perpendicular to a planar orientation of the metal surface immediately adjacent the RF plate.

7. The implantable medical device of claim 6, wherein the extension member is folded around the plate, and the plate is sandwiched between the extension member and metal surface.

8. The implantable medical device of claim 1, wherein the dielectric material includes at least one of a thermosetting polymer, an epoxy, thermoplastic, polyurethane, tecothane, pellethane, silicone, acrylic or bionate.

* * * * *